United States Patent
Yagi et al.

(10) Patent No.: US 9,937,127 B2
(45) Date of Patent: Apr. 10, 2018

(54) METHOD OF PRODUCING FINE PARTICLES SURFACE-MODIFIED WITH WATER-SOLUBLE SUBSTANCE

(75) Inventors: Nobuhiro Yagi, Sunto-gun (JP); Hiroko Sugishita, Sunto-gun (JP); Masashi Nakakura, Mishima (JP); Hiroko Kusano, Sunto-gun (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 294 days.

(21) Appl. No.: 11/883,169

(22) PCT Filed: Jan. 27, 2006

(86) PCT No.: PCT/JP2006/301343
§ 371 (c)(1),
(2), (4) Date: Jul. 27, 2007

(87) PCT Pub. No.: WO2006/080452
PCT Pub. Date: Aug. 3, 2006

(65) Prior Publication Data
US 2008/0145414 A1    Jun. 19, 2008

(30) Foreign Application Priority Data
Jan. 28, 2005 (JP) ................ 2005-022241

(51) Int. Cl.
*A61K 9/127* (2006.01)
*A61K 9/107* (2006.01)
*B01J 13/02* (2006.01)
*A61K 9/00* (2006.01)

(52) U.S. Cl.
CPC ............ *A61K 9/1271* (2013.01); *A61K 9/107* (2013.01); *B01J 13/02* (2013.01); *A61K 9/0019* (2013.01)

(58) Field of Classification Search
CPC ........ A47F 3/145; A61K 9/0019; A61K 9/107; A61K 9/1271; B01J 13/02
USPC .......................................... 424/450; 514/784
See application file for complete search history.

(56) References Cited

U.S. PATENT DOCUMENTS

| | | | |
|---|---|---|---|
| 5,013,556 A | 5/1991 | Woodle et al. | |
| 5,593,622 A | 1/1997 | Yoshioka et al. | |
| 5,676,971 A | 10/1997 | Yoshioka et al. | |
| 5,846,458 A | 12/1998 | Yoshioka et al. | |
| 2004/0022938 A1* | 2/2004 | Kato et al. | 427/212 |

FOREIGN PATENT DOCUMENTS

| | | |
|---|---|---|
| JP | 2-149512 | 6/1990 |
| JP | 3-181415 | 8/1991 |
| JP | 5-501264 | 3/1993 |
| JP | 6-298638 | 10/1994 |
| JP | 7-173052 | 7/1995 |

* cited by examiner

*Primary Examiner* — Janet L Epps-Smith
(74) *Attorney, Agent, or Firm* — Wenderoth, Lind & Ponack, L.L.P.

(57) ABSTRACT

An object of the present invention is to provide a method of easily producing fine particles comprising a lipid, a fatty acid, or a derivative thereof, surface-modified with a water-soluble substance, etc. There are provided a method of producing a fine particles, surface-modified with a water-soluble substance, which contains the process of dispersing fine particles comprising a lipid, a fatty acid, or a derivative thereof, and dissolving or dispersing a surface modifier which is a lipid derivative, a fatty acid derivative, or an aliphatic hydrocarbon derivative of a water-soluble substance, in a liquid containing a polar organic solvent, and the like.

28 Claims, 2 Drawing Sheets

METHOD OF PRODUCING FINE PARTICLES SURFACE-MODIFIED WITH WATER-SOLUBLE SUBSTANCE

This application is a U.S. national stage of International Application No. PCT/JP2006/301343 filed Jan. 27, 2006.

TECHNICAL FIELD

The present invention relates to a method of producing fine particles comprising a lipid, a fatty acid, or a derivative thereof surface-modified with a water-soluble substance.

BACKGROUND ART

It has been known in the fields of pharmaceutical products, agrochemicals, food products, and the like, that, by surface-modifying fine particles comprising an active ingredient with a water-soluble substance, or by chemically modifying an active ingredient with a water-soluble substance, the active ingredient can be suppressed from approaching to or being recognized by a protein, etc. in a living body, and thus an effect of prolonging half-life in blood, reducing antigenicity, etc. can be obtained. Further, it is known that, also in the case of fine particles comprising a lipid, a fatty acid, or a derivative thereof, such as liposome and emulsion particles, the effect of prolonging half-life in blood, reducing antigenicity, etc. can be obtained by surface-modifying the fine particles with a water-soluble substance (see Patent Documents 1 and 2).

The surface modification of the fine particles comprising the lipid, fatty acid, or derivative thereof with the water-soluble substance is carried out generally such that, in the method of producing the fine particles, at least a constituent component capable of forming particles among the constituent component is placed under the presence of a surface modifier which is a derivative of the water-soluble substance, so that the constituent component capable of forming particles and the surface modifier form the fine particles in combination (see Patent Document 2). However, when the fine particles are modified with a large amount of the surface modifier in the above process, the physicochemical properties of the fine particles may change, whereby the desired surface-modification of the fine particles may not be achieved in some cases. For example, it is known that, when a phospholipid is used under the presence of a large amount of a polyethylene glycol derivative for preparing liposome, the phospholipid forms not a lipid membrane but a micelle (see *Biophysical Journal,* 1997, vol. 73, p. 258-266, and *Biophysical Journal,* 2002, vol. 83, p. 2419-2439). Further, in the surface modification of the fine particles with the water-soluble substance, though it is only necessary to modify the outer surface of the fine particles from the viewpoint of the above mentioned purpose, the surface modifier is undesirably contained inside the fine particles in the method of using the particle component under the presence of the surface modifier for forming the fine particles.

Methods of modifying only the outer surface of the fine particles with the water-soluble substance are known (see Patent Documents 1 and 3), such as the method which forms the fine particles by using at least the constituent component capable of forming the particles among the constituent components of the fine particles comprising the lipid, fatty acid, or derivative thereof, and then the surface modifier which is a lipid derivative, fatty acid derivative, or aliphatic hydrocarbon derivative of the water-soluble substance is added to the fine particles. In the method of Patent Document 1, a polyethylene glycol-bonded phospholipid is added to liposome in water at room temperature, to surface-modify the liposome with the polyethylene glycol. To sufficiently achieve surface modification at a temperature of room temperature or lower in this method, it is only limited to the case when a phospholipid having a low phase transition temperature is used as the constituent component capable of forming the particles in the liposome in combination with a surface modifier having a high critical micelle concentration, as described also in Patent Document 3. Further, in the method described in Patent Document 3, a surface modifier which is a compound, which has a hydrophobic moiety at one end and has a hydrophilic moiety at the other end, is added to liposome in water, and the mixture is heated at the phase transition temperature of the constituent component capable of forming particles or higher, to surface-modify the liposome.

Patent Document 1: Japanese Published Unexamined Patent Application No. 149512/90
Patent Document 2: Japanese Translation of PCT International Application No. 501264/93
Patent Document 3: Japanese Published Unexamined Patent Application No. 181415/91

DISCLOSURE OF THE INVENTION

Problems to be Solved by the Invention

An object of the present invention is to provide a method of easily producing fine particles comprising a lipid, a fatty acid, or a derivative thereof surface-modified with a water-soluble substance, etc.

Problems to be Solved by the Invention

The present invention relates to the following (1) to (17).
(1) A method of producing fine particles, surface-modified with a water-soluble substance, which comprises the Step A of dispersing fine particles comprising a lipid, a fatty acid, or a derivative thereof, and dissolving or dispersing a surface modifier which is a lipid derivative, a fatty acid derivative, or an aliphatic hydrocarbon derivative of the water-soluble substance, in a liquid containing a polar organic solvent.
(2) The method according to the above (1), wherein a polar organic solvent in which the surface modifier is soluble is used as the polar organic solvent.
(3) The method according to the above (1), wherein one or more solvent(s) selected from alcohols, glycols, and polyalkylene glycols is used as the polar organic solvent.
(4) The method according to any one of the above (1) to (3) wherein a liquid containing the polar organic solvent in which a concentration of the polar organic solvent is 80 vol % or less is used as the liquid containing a polar organic solvent.
(5) The method according to any one of the above (1) to (4), wherein the fine particles comprising a lipid, a fatty acid, or a derivative thereof are fine particles coated with the lipid, the fatty acid, or the derivative thereof.
(6) The method according to any one of the above (1) to (5), wherein in the Step A, an amphiphilic substance is dissolved or dispersed in the liquid comprising a polar organic solvent.
(7) The method according to the above (6), wherein the weight ratio between the amphiphilic substance and the surface modifier is 10:1 to 1:100.
(8) The method according to the above (6) or (7), wherein the amphiphilic substance is one or more substance(s)

selected from phospholipids, glycoglycerolipids, glycosphingolipids, cholesterols, cationic lipids, anionic lipids, surfactants, and lipid or fatty acid derivatives of water-soluble polymers.

(9) The method according to any one of the above (1) to (8), wherein the fine particles comprising a lipid, a fatty acid, or a derivative thereof are fine particles comprising one or more component(s) selected from a lipid assembly, liposome, and emulsion particles as a constituent component.

(10) The method according to any one of the above (1) to (9), wherein the surface modifier is one or more component (s) selected from polyethylene glycolated lipids, polyglycerolated lipids, polyethylene glycol alkyl ethers, polyethylene glycol sorbitan fatty acid esters, polyethylene glycol fatty acid esters, and polyglycerol fatty acid esters.

(11) The method according to the above (6) or (7), wherein the fine particles comprising a lipid, a fatty acid, or a derivative thereof are liposome, the polar organic solvent is ethanol, the amphiphilic substance is a phospholipid, and the surface modifier is a polyethylene glycolated lipid.

(12) The method according to the above (6) or (7), wherein the fine particles comprising a lipid, a fatty acid, or a derivative thereof are liposome, the polar organic solvent is ethanol, the amphiphilic substance is a phospholipid, and the surface modifier is a polyethylene glycol fatty acid ester.

(13) A kit for preparing the fine particles comprising a lipid, a fatty acid, or a derivative thereof surface-modified by the method described in any one of claims 1 to 12, which comprises at least fine particles comprising the lipid, the fatty acid, or the derivative thereof, a surface modifier which is a lipid derivative, a fatty acid derivative, or an aliphatic hydrocarbon derivative of a water-soluble substance, and a liquid containing a polar organic solvent.

(14) Fine particles comprising a lipid, a fatty acid, or a derivative thereof, surface-modified with a water-soluble substance, obtainable by the method described in any one of the above (1) to (12).

(15) A therapeutic agent for tumor, which comprises the fine particles comprising a lipid, a fatty acid, or a derivative thereof, surface-modified with a water-soluble substance, obtainable by the method described in any one of the above (1) to (12), wherein the fine particles contain an antitumor drug.

(16) A therapeutic agent for inflammation, which comprises the fine particles comprising a lipid, a fatty acid, or a derivative thereof, surface-modified with a water-soluble substance, obtainable by the method described in any one of the above (1) to (12), wherein the fine particles contain an anti-inflammatory drug.

(17) A carrier comprising drug for a tumor site or an inflammation site, which comprises the fine particles comprising a lipid, a fatty acid, or a derivative thereof, surface-modified with a water-soluble substance, obtainable by the method described in any one of the above (1) to (12), wherein the fine particles contains the drug.

Effect of the Invention

According to the present invention, there are provided a method of easily producing fine particles comprising a lipid, a fatty acid, or a derivative thereof surface-modified with a water-soluble substance, and the like. Further, there are provided a method of producing a fine particles comprising a lipid, a fatty acid, or a derivative thereof surface-modified with the water-soluble substance, which is capable of modifying various types of modification target particles substantially without heating, and the like.

BEST MODE FOR CARRYING OUT THE INVENTION

Figure 1:
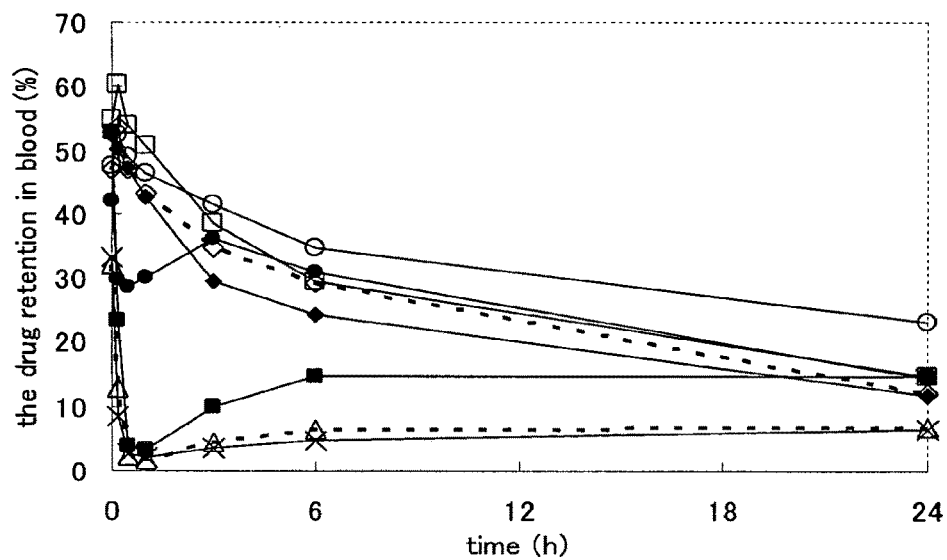
FIG. 1 Blood kinetics of preparations obtained in Examples 1 to 5 and Comparative Examples 1 to 3 after administering them to rats are shown. The closed squares represent administration results of the preparation of Example 1, the open squares represent administration results of the preparation of Example 2, the closed circles represent administration results of the preparation of Example 3, the open circles represent administration results of the preparation of Example 4, the closed diamonds represent administration results of the preparation of Example 5, x-marks represent administration results of the preparation of Comparative Example 1, the open triangles represent administration results of the preparation of Comparative Example 2 and the open diamonds represent administration results of the preparation of Comparative Example 3.

In the present invention, the fine particles comprising the lipid, fatty acid, or derivative thereof which are surface-modified with the water-soluble substance, are such that the fine particles comprising the lipid, fatty acid, or derivative thereof as modification target particles are modified with the lipid derivative, fatty acid derivative, or aliphatic hydrocarbon derivative of the water-soluble substance as surface modifier. The term "surface modification" used in the present invention means that the surface modifier is contained in the modification target particles such that one part (generally a lipid, fatty acid, or aliphatic hydrocarbon moiety) of the surface modifier is introduced to the inside of the surface of modification target particles, and the remaining part (generally a water-soluble substance moiety) protrudes from the particle surface.

The lipid used in the present invention may be a simple lipid, a complex lipid, or a derived lipid, and examples thereof include phospholipids, glycoglycerolipids, glycosphingolipids, sphingoids, sterols, cationic lipid, and the like, and preferred examples thereof include phospholipids, cationic lipids, and the like. Examples of the lipid derivatives include surfactants (having the same definitions as described hereinafter), polymers (having the same definitions as described hereinafter, specifically dextrans, etc.), polyoxyethylenes and derivatives thereof (specifically polyethylene glycols, etc.), oligoglycerins and derivatives thereof, and the like, preferred examples thereof include polyethylene glycol-modified phospholipids.

Examples of the phospholipid include natural and synthetic phospholipids such as phosphatidylcholine (specifically, soybean phosphatidylcholine, egg yolk phosphatidylcholine (EPC), distearoyl phosphatidylcholine, dipalmitoyl phosphatidylcholine, dimyristoyl phosphatidylcholine, dioleoyl phosphatidylcholine, etc.), phosphatidylethanolamine (specifically, distearoyl phosphatidylethanolamine (DSPE), dipalmitoyl phosphatidylethanolamine, dioleoyl phosphatidylethanolamine, etc.), glycerophospholipid (specifically, phosphatidylserine, phosphatidic acid, phosphatidylglycerol, phosphatidylinositol, lysophosphatidylcholine, etc.) sphingophospholipid (specifically sphingomyelin, ceramide phosphoethanolamine, ceramide phosphoglycerol, ceramide phosphoglycerophosphate, etc.) glycerophosphono lipid, sphingophosphonolipid, natural lecithin (specifically, egg yolk lecithin, soybean lecithin, etc.) and hydrogenated phospholipid (specifically hydrogenated phosphatidylcholine, etc.).

Examples of the glyceroglycolipid include sulfoxyribosyl glyceride, diglycosyl diglyceride, digalactosyl diglyceride, galactosyl diglyceride, glycosyl diglyceride and the like.

Examples of the sphingoglycolipid include galactosyl cerebroside, lactosyl cerebroside, ganglioside and the like.

Examples of the sphingoid include sphingan, icosasphingan, sphingosine, a derivative thereof and the like. Examples of the derivative thereof include those in which —$NH_2$ of sphingan, icosasphingan, sphingosine or the like is replaced with —$NHCO(CH_2)_xCH_3$ (in the formula, x represents an integer of 0 to 18, in particular, 6, 12 or 18 is preferred) and the like.

Examples of the sterol include cholesterol, dihydrocholesterol, lanosterol, β-sitosterol, campesterol, stigmasterol, brassicasterol, ergocasterol, fucosterol, 3β-[N—(N'N'-dimethylaminoethyl)carbamoyl cholesterol (DC-Chol) and the like.

Examples of the cationic lipid include N-[1-(2,3-dioleoylpropyl)]-N,N,N-trimethylammonium chloride (DOTAP), N-[1-(2,3-dioleoylpropyl)]-N,N-dimethylamine (DODAP), N-[1-(2,3-dioleyloxypropyl)-N,N,N-trimethylammonium chloride (DOTMA), 2,3-dioleyloxy-N-[2-(sperminecarboxyamido)ethyl]-N,N-dimethyl-1-propanaminium trifluoroacetate (DOSPA), N-[1-(2,3-ditetradecyloxypropyl)]-N,N-dimethyl-N-hydroxyethylammonium bromide (DMRIE), N-[1-(2,3-dioleyloxypropyl)]-N,N-dimethyl-N-hydroxyethylammonium bromide (DORIE) and the like.

Examples of the fatty acids and the derivatives thereof used in the present invention include fatty acids such as stearic acid, palmitic acid, and lauric acid, and surfactants prepared by chemically binding fatty acids to other substances, and the like.

Examples of the surfactants include polyoxyethylene sorbitan monooleates (specifically polysorbate 80, etc.), sorbitan fatty acids (specifically sorbitan monolaurate, sorbitan monooleate, etc.), polyoxyethylene derivatives (specifically polyoxyethylene hardened castor oil 60, etc.), glycerin fatty acid esters, and the like.

In the present invention, the fine particles comprising the lipid, fatty acid, or derivative thereof may be fine particles comprising a lipid assembly, liposome, emulsion particles, or the like, or fine particles comprising a drug, a polymer, a metal colloid, fine particles preparation, or the like, and may be fine particles comprising the lipid, fatty acid, or derivative thereof. The fine particles preferably comprise a lipid assembly, liposome, an emulsion, or the like, more preferably comprise liposome. The fine particles comprising the lipid assembly, liposome, emulsion particles or the fine particles comprising a drug, a polymer, a metal colloid, fine particles preparation, or the like and comprising the above-mentioned lipid, fatty acid or the derivative thereof may be fine particles comprising a complex of combining two or more selected from a drug, a lipid assembly, liposome, emulsion particles, polymer, a metal colloid and fine particles preparation, or fine particles comprising a complex of combining one or more selected from a drug, a lipid assembly, liposome, emulsion particles, a polymer, a metal colloid and fine particles preparation, with another compound such as a saccharide, a lipid, or an inorganic compound, as long as the fine particles contain the above lipid, fatty acid, or derivative thereof. The fine particles preferably comprise a complex of the drug and one or more selected from the lipid assembly, liposome and emulsion particles, more preferably comprise a complex of the drug and the liposome.

The fine particles comprising the lipid, fatty acid, or derivative thereof, which comprises the lipid assembly, liposome, emulsion particle, or the like, or the drug, polymer, metal colloid, fine particles preparation, or the like, may be fine particles coated with the lipid, fatty acid, or derivative thereof. For example, fine particles comprising the drug, lipid assembly, liposome, emulsion particle, polymer, metal colloid, fine particles preparation, or the like may be coated with the lipid, fatty acid, or derivative thereof to form the fine particles. The fine particles are more preferably provided by coating the fine particles comprising the lipid assembly, liposome, or emulsion particle with the lipid, fatty acid, or derivative thereof. The fine particles coated with the lipid, fatty acid, or derivative thereof may be provided by coating fine particles comprising the above-mentioned complex with the lipid, fatty acid, or derivative thereof.

In the fine particles coated with the lipid, fatty acid, or derivative thereof, the coating component of the lipid, fatty acid, or derivative thereof is preferably a lipid, a fatty acid, or a derivative thereof capable of forming a lipid membrane, and examples thereof include the above-described lipids, surfactants, and the like. The coating component is more preferably a neutral lipid among the above lipids and surfactants, further preferably a phospholipid, most preferably an EPC. It is preferred that the lipid, fatty acid, or derivative thereof used for coating is soluble in the polar organic solvent, and it is preferred that a liquid in which constituent component of the lipid membrane can be dispersed and comprising the polar organic solvent at a concentration capable of dispersing the complex particles is in the liquid comprising polar organic solvent. The neutral lipids include lipids other than the above cationic lipids, and cationic surfactants, anionic lipids, and anionic surfactants to be hereinafter described, among the above lipids and surfactants. More preferred examples of the neutral lipids include phospholipids, glycoglycerolipids, glycosphingolipids, and the like.

The drug used in the present invention may be a drug available in the form of fine particles in the liquid comprising a polar organic solvent in the Step A, a drug which forms a complex with another component constituting the fine particles comprising the lipid, fatty acid or derivative thereof, and available in the form of fine particles in the solvent, and the like. For example, the drug may be substances having pharmacological activity among a protein, a peptide, a nucleic acid, a low-molecular compound, a saccharide, a polymer, a lipid compound, a metal compound, and the like. Preferred examples include a nucleic acid, and more preferred examples include one or more substance(s) selected from a gene, DNA, RNA, an oligonucleotide (ODN), plasmid, and siRNA.

Examples of the protein or the peptide include bradykinin, angiotensin, oxytocin, vasopressin, adrenocorticotropin, calcitonin, insulin, glucagon, cholecystokinin, β-endorphin, melanocyte inhibiting factor, melanocyte stimulating hormone, gastrin antagonist, neurotensin, somatostatin, brucine, cyclosporine, enkephalin, transferrin, Arg-Gly-Asp (RGD) peptide, thyroid hormone, growth hormone, gonadotropic hormone, luteinizing hormone, asparaginase, arginase, uricase, carboxypeptidase, glutaminase, superoxide dismutase, tissue plasminogen activator, streptokinase, interleukin, interferon, muramyl dipeptide, thymopoietin, granulocyte colony stimulating factor, granulocyte macrophage colony stimulating factor, erythropoietin, thrombopoietin, trypsin inhibitor, lysozyme, epidermal growth factor (EGF), insulin-like growth factor, nerve growth factor, platelet-derived growth factor, transforming growth factor, endothelial cell growth factor, fibroblast growth factor, glial growth factor, thymosin and specific antibody (such as anti-EGF receptor antibody) and the like.

Examples of the nucleic acid include ODN such as an antisense oligonucleotide and a sense oligonucleotide, a gene, DNA, RNA, plasmid, siRNA and the like. The nucleic acid includes derivatives in which an oxygen atom or the like contained in a phosphate moiety or an ester moiety in the nucleic acid structure has been substituted with another atom such as a sulfur atom. Incidentally, siRNA means a short double-stranded RNA.

Examples of the low-molecular compound include e-aminocaproic acid, arginine hydrochloride, potassium L-aspartate, tranexamic acid, bleomycin sulfate, vincristine sulfate, cefazolin sodium, cephalothin sodium, citicoline, cytarabine, gentamicin sulfate, vancomycin hydrochloride, kanamycin sulfate, amikacin sulfate and the like.

Examples of the saccharide include sodium chondroitin sulfate, heparin sodium, dextran fluorescein and the like.

Examples of the polymer include sodium polyethylene sulfonate, a copolymer of divinyl ether with maleic anhydride (DIVEMA), a bonded product of a styrene-maleic anhydride copolymer with neocarzinostatin (SMANCS) and the like.

Examples of the lipid compound include vitamin D, vitamin. E, and the like. Examples of the metal compound include cisplatin, and the like.

The lipid assembly and the liposome used in the present invention comprise the above-mentioned lipid, fatty acid, or derivative thereof. The lipid, fatty acid, or derivative thereof may be used singly or in combination with another one, and is preferably used in combination. Examples of the combinations include combinations of two or more components selected from hydrogenated soybean phosphatidylcholines, polyethylene glycol-modified phospholipids, and cholesterols, combinations of two or more components selected from distearoylphosphatidylcholines, polyethylene glycol-modified phospholipids, and cholesterols, combinations of EPC and DOTAP, combinations of two or more components selected from EPC, DOTAP, and polyethylene glycol-modified phospholipids, combinations of two or more components selected from EPC, DOTAP, cholesterols, and polyethylene glycol-modified phospholipids, and the like.

Further, the liposome may contain a membrane stabilizer such as a sterol including cholesterol, an antioxidant such as tocopherol or the like, as needed.

Examples of the lipid assembly in the present invention include a spherical micelle, a spherical reversed micelle, a sausage-shaped micelle, a sausage-shaped reversed micelle, a plate-shaped micelle, a plate-shaped reversed micelle, hexagonal I, hexagonal II and an associated product comprising two or more lipid molecules.

Examples of the emulsion particles in the present invention include oil-in-water (o/w) emulsion particles such as a fat emulsion, an emulsion composed of a nonionic surfactant and soybean oil, lipid emulsion and lipid nanosphere, water-in-oil-in-water (w/o/w) emulsion particles and the like.

Examples of the polymer in the present invention include natural polymers such as albumin, dextran, chitosan, dextran sulfate and DNA, synthetic polymers such as poly-L-lysine, polyethyleneimine, polyaspartic acid, a copolymer of styrene with maleic acid, a copolymer of isopropylacrylamide with acrylpyrrolidone, PEG-modified dendrimer, polylactic acid, polylactic acid polyglycolic acid and polyethylene glycolated polylactic acid, a salt thereof and the like.

Here, the salt of the polymer includes, for example, a metal salt, an ammonium salt, an acid addition salt, an organic amine addition salt, an amino acid addition salt and the like. Examples of the metal salt include alkali metal salts such as a lithium salt, a sodium salt and a potassium salt, alkaline earth metal salts such as a magnesium salt and a calcium salt, an aluminum salt, a zinc salt and the like. Examples of the ammonium salt include salts of ammonium, tetramethylammonium and the like. Examples of the acid addition salt include inorganates such as a hydrochlorate, a sulfate, a nitrate and a phosphate, and organates such as an acetate, a maleate, a fumarate and a citrate. Examples of the organic amine addition salt include addition salts of morpholine, piperidine and the like, and examples of the amino acid addition salt include addition salts of glycine, phenylalanine, aspartic acid, glutamic acid, lysine and the like.

Examples of the metal colloid in the present invention include metal colloids including gold, silver, platinum, copper, rhodium, silica, calcium, aluminum, iron, indium, cadmium, barium, lead and the like.

Examples of the fine particles preparation in the present invention include a microsphere, a microcapsule, a nanocrystal, lipid nanoparticles, a polymeric micelle and the like.

In the present invention, when the fine particles comprising the lipid, fatty acid, or derivative thereof comprise a complex of the drug and one or more component(s) selected from a lipid assembly, liposome, emulsion particles, a polymer, a metal colloid and fine particles preparation, it is more preferred that the lipid assembly, liposome, emulsion particles, polymer, metal colloid or fine particles preparation has an electrostatic charge opposite to that of the drug. In order for a lipid assembly, liposome, emulsion particles, a polymer, a metal colloid, and fine particles preparation to have the electrostatic charge opposite to that of the drug, a lipid assembly, liposome, emulsion particles, a polymer, a metal colloid, and fine particles preparation preferably comprises a charged substance having the electrostatic charge opposite to that of the drug, and more preferably comprises a lipid having the electrostatic charge opposite to that of the drug (the above-described cationic lipid or the anionic lipid to be hereinafter described).

The charged substance having the electrostatic charge opposite to that of the drug such as a lipid assembly, liposome, emulsion particles, a polymer, a metal colloid, and fine particles preparations may be classified into a cationic substance exhibiting a cationic property and an anionic substance exhibiting an anionic property. However, even if it is a zwitterionic substance having both of cationic group and anionic group, the relative electronegativity changes depending on the pH, bonding with another substance or the like, and it can be classified into a cationic substance or an anionic substance depending on the conditions. Such a charged substance may be used as a constituent component of the above-mentioned fine particles or may be used by adding it to the constituent component of the above-mentioned fine particles.

Examples of the cationic substance include the cationic substances among those illustrated in the above-mentioned definition of the above-mentioned fine particles [specifically, a cationic lipid (the same definition as above), a cationic sterol, a cationic polymer], a cationic surfactants, a protein or a peptide with which a complex can be formed at a pH equal to or less than an isoelectric point, and the like.

Examples of the cationic sterols include DC-Chol, and the like.

Examples of the cationic polymer include poly-L-lysine, polyethyleneimine, polyfect, chitosan and the like.

Examples of the cationic surfactants include an alkylamine salt, an acylamine salt, a quaternary ammonium salt, an amine derivative and the like. Specific examples include benzalkonium chloride, an acylaminoethyldiethylamine salt, an N-alkylpolyalkylpolyamine salt, a polyethylene polyamide of fatty acid, cetyltrimethylammonium bromide, dodecyltrimethylammonium bromide, alkylpolyoxyethyleneamine, N-alkylaminopropylamine, a triethanolamine fatty acid ester and the like.

The protein or the peptide with which a complex can be formed at a pH equal to or less than an isoelectric point is not particularly limited as long as it is a protein or a peptide with which a complex can be formed at a pH equal to or less than the isoelectric point of the substance. Examples thereof include albumin, orosomucoid, globulin, fibrinogen, pepsin, ribonuclease T1 and the like.

Examples of the anionic substance include the anionic substances among those illustrated in the above-mentioned definition of the fine particles (specifically, an anionic lipid, an anionic polymer and the like), an anionic surfactants, a protein or a peptide, with which a complex can be formed at a pH equal to or greater than an isoelectric point, a nucleic acid and the like.

Examples of the anionic lipid include phosphatidylserine, phosphatidylglycerol, phosphatidylinositol, phosphatidic acid and the like.

Examples of the anionic polymer include polyaspartic acid, a copolymer of styrene with maleic acid, a copolymer of isopropylacrylamide with acrylpyrrolidone, PEG-modified dendrimer, polylactic acid, polylactic acid polyglycolic acid, polyethylene glycolated polylactic acid, dextran sulfate, sodium dextran sulfate, chondroitin sulfate, sodium chondroitin sulfate, hyaluronic acid, chondroitin, dertaman sulfate, heparan sulfate, heparin, ketaran sulfate, dextran fluorescein anionic and the like.

Examples of the anionic surfactants include acylsarcosine, sodium alkylsulfate, alkylbenzene sulfonate, a sodium fatty acid having 7 to 22 carbon atoms and the like. Specific examples include sodium dodecyl sulfate, sodium lauryl sulfate, sodium cholate, sodium deoxycholate, sodium taurodeoxycholate and the like.

The protein or the peptide with which a complex can be formed at a pH equal to or greater than an isoelectric point is not particularly limited as long as it is a protein or a peptide with which a complex can be formed at a pH equal to or greater than the isoelectric point of the substance. Examples thereof include albumin, orosomucoid, globulin, fibrinogen, histone, protamine, ribonuclease, lysozyme and the like.

Examples of the nucleic acid as an anionic substance include DNA, RNA, plasmid, siRNA, ODN and the like. It may have any length and any sequence as long as it does not exhibit a physiological activity.

The fine particles comprising a lipid, a fatty acid, or a derivative thereof in the present invention can be produced by or in accordance with a known production method, and may be produced by any production method. For example, in the production of the fine particles comprising, as a constituent component, liposome, which is one of the fine particles, a known liposome preparation method can be applied. As the known liposome preparation method, for example, liposome preparation method by Bangham, et al. [see "Journal of Molecular Biology" (J. Mol. Biol.), vol. 13, pp. 238-252 (1965)], an ethanol injection method [see "Journal of Cell Biology" (J. Cell Biol.), vol. 66, pp. 621-634 (1975)], a French press method [see "FEBS Letters" (FEBS Lett.), vol. 99, pp. 210-214 (1979)], a freeze-thaw method [see "Archives of Biochemistry and Biophysics" (Arch. Biochem. Biophys.), vol. 212, pp. 186-194 (1981)], a reverse phase evaporation method [see "Proceedings of the National Academy of Science United States of America" (Proc. Natl. Acad. Sci. USA), vol. 75, pp. 4194-4198 (1978)], a pH gradient method (see, for example, Japanese Patent No. 2,572,554, Japanese Patent No. 2,659,136, etc.) and the like. As a solution for dispersing liposome in the production of the liposome, for example, water, an acid, an alkali, any of various buffers, a physiological saline solution, an amino acid infusion or the like can be used. Further, in the production of the liposome, it is also possible to add an antioxidant such as citric acid, ascorbic acid, cysteine or ethylenediamine tetraacetic acid (EDTA), an isotonic agent such as glycerol, glucose, sodium chloride or the like. Further, the liposome can be prepared by dissolving lipid or the like in, for example, an organic solvent such as ethanol, distilling off the solvent, adding a physiological saline solution or the like and stirring the mixture by shaking, thereby forming liposome.

An average particle diameter of the liposome can be freely selected upon demand. Examples of a method of adjusting the average particle diameter include an extrusion method and a method in which a large multilamellar liposome vesicle (MLV) is mechanically pulverized (specifically using Manton-gaulin, a microfluidizer or the like) [see "Emulsion and Nanosuspensions for the Formulation of Poorly Soluble Drugs", edited by R. H. Muller, S. Benita and B. Bohm, Scientific Publishers, Stuttgart, Germany, pp. 267-294 (1998)] and the like.

In addition, the method of producing a complex obtained by combining two or more substances selected from, for example, a drug, a lipid assembly, liposome, emulsion particles, a polymer, a metal colloid, fine particles preparation and the like, which constitute the fine particles comprising a lipid, a fatty acid, or a derivative thereof (specific examples include a complex of liposome or a lipid assembly comprising a cationic lipid and a nucleic acid, a complex of a polymer comprising a cationic polymer such as poly-L-lysine and a nucleic acid, a complex of liposome or a lipid assembly comprising an anionic lipid such as phosphatidic acid and a protein, a complex of a polymer comprising an anionic polymer such as styrene-maleic acid and a protein, a complex of liposome or a lipid assembly comprising a cationic lipid and a protein, a complex of a polymer comprising a cationic polymer such as poly-L-lysine and a protein and the like) may be, for example, a production method in which a drug is simply mixed with a lipid assembly, liposome, a polymer or the like in water. At this time, a sieve step, a sterilization step or the like can be further added as needed. Further, it is also possible to perform the formation of the complex in any of various solvents such as acetone and ether. For example, a nucleic acid and a lipid are dissolved in an organic solvent such as ethanol, the solvent is distilled off, a physiological saline solution or the like is added thereto, and the mixture is stirred by shaking, whereby a nucleic acid complex can also be formed. As another method of forming a complex, for example, liposome is prepared using a cationic substance and a polyethylene glycolated lipid [specifically, polyethylene glycol phosphatidyl ethanolamine (more specifically, 1,2-distearoyl-sn-glycero-3-phosphoethanolamine-N-[methoxy(polyethylene glycol)-2000] (PEG-DSPE) or the like), polyoxyethylene hydrogenated castor oil 60, Cremophor EL and the like] or the like in water, then, for example, a nucleic acid is added thereto, and further an anionic polymer is added thereto, whereby a multicomplex can also be formed.

Among the fine particles comprising the lipid, fatty acid or derivative thereof in the present invention, the fine particles coated with the lipid, fatty acid, or derivative thereof may be produced by any method, and may be produced by a known method or a modified method thereof. For example, the fine particles comprising the drug, lipid assembly, liposome, emulsion particle, polymer, metal colloid, fine particles preparation, and the like may be coated with the lipid, fatty acid, or derivative thereof by a method described in WO 02/28367, etc.

The average particle diameter of the fine particles comprising the lipid, fatty acid, or derivative thereof used in the invention is preferably 300 nm or less, more preferably 200 nm or less, and for example, the size of the fine particles is preferably such that the fine particles can be administered by injection.

There are no particular limitations on the polar organic solvent used in the present invention, and the polar organic solvent is preferably such that the surface modifier is soluble therein. Examples of the polar organic solvents usable in the present invention include alcohols such as methanol, ethanol, n-propanol, 2-propanol, n-butanol, 2-butanol, and tert-butanol; glycols such as glycerin, ethylene glycol, and propylene glycol; polyalkylene glycols such as polyethylene glycol, polyoxyethylene hardened castor oil, and polyoxyethylene sorbitan fatty acid ester or ether; and the like. The polar organic solvent is preferably ethanol.

As a lipid derivative, a fatty acid derivative or a aliphatic hydrocarbon derivative of the water-soluble substance in the present invention, for example, lipid derivative, fatty acid derivative, or aliphatic hydrocarbon derivative of one or more substance(s) selected from saccharides, peptides, nucleic acids, and water-soluble polymers, or the like may be used. Preferred examples thereof include glycolipids, or lipid derivatives or fatty acid derivatives of water-soluble polymers, more preferred examples thereof include lipid derivatives or fatty acid derivatives of water-soluble polymers, further preferred examples thereof include polyethylene glycolated lipids, polyglycerolated lipids, polyethylene glycol alkyl ethers, polyethylene glycol sorbitan fatty acid esters, polyethylene glycol fatty acid esters, and polyglycerol fatty acid esters.

In the present invention, it is preferred that a moiety of the molecule of the lipid derivative, fatty acid derivative, or aliphatic hydrocarbon derivative of the water-soluble substance has a property which can bound to the constituent component of the fine particles comprising the lipid, fatty acid, or derivative thereof due to the hydrophobic affinity, electrostatic interaction, or the like. It is more preferred that the moiety can bound to the lipid, fatty acid, or derivative thereof in the fine particles due to the hydrophobic affinity, electrostatic interaction, or the like.

For example, the lipid derivative of the water-soluble substance may be such that the water-soluble substance is bound to the above-mentioned lipid or derivative thereof. For example, the fatty acid derivative of the water-soluble substance may be such that the water-soluble substance is bound to a fatty acid such as stearic acid, palmitic acid, myristic acid, or lauric acid. Further, for example, the aliphatic hydrocarbon derivative of the water-soluble substance may be such that the water-soluble substance is bonded to an alcoholic residue of a long-chain aliphatic alcohol, a polyoxypropylene alkyl, or a glycerin fatty acid ester, or the like.

Examples of the lipid derivative, fatty acid derivative or aliphatic hydrocarbon derivative of the saccharide, peptide, or nucleic acid include the above-mentioned lipid derivatives, fatty acid derivatives or aliphatic hydrocarbon derivatives of the water-soluble substance, wherein the water-soluble substance being a saccharide such as sucrose, sorbitol, or lactose, a peptide such as a casein-derived peptide, an egg white-derived peptide, a soybean-derived peptide, or a glutathione, or a nucleic acid such as DNA, RNA, plasmid, siRNA, or ODN. More specific examples of the saccharide lipid derivatives include glycolipids such as the above glycoglycerolipids and the above-mentioned glycosphingolipids, and the like.

Examples of the lipid derivative, fatty acid derivative or aliphatic hydrocarbon derivative of the water-soluble polymer include the above-mentioned lipid derivatives, fatty acid derivatives, or aliphatic hydrocarbon derivatives of the water-soluble substance, wherein the water-soluble substance being a polyethylene glycol, a polyglycerin, a polyethyleneimine, a polyvinyl alcohol, a polyacrylic acid, a polyacrylamide, an oligosaccharide, a dextrin, a water-soluble cellulose, a dextran, a chondroitin sulfate, a polyglycerin, a chitosan, a polyvinyl pyrolidone, a polyaspartic acid amide, a poly-L-lysine, a mannan, a pullulan, an oligoglycerol, a derivative thereof, or the like. More preferred examples include polyethylene glycol derivatives, polyglycerin derivatives, and the like, and further preferred examples include polyethylene glycol derivatives.

Examples of the lipid derivative, fatty acid derivative or aliphatic hydrocarbon derivative of polyethylene glycol derivative include polyethylene glycolated lipids (specifically polyethylene glycol-phosphatidylethanolamines (more specifically PEG-DSPE, etc.), polyoxyethylene, hardened castor oil 60, Cremophor EL, etc.), polyethylene glycol alkyl ethers, polyethylene glycol sorbitan fatty acid esters (specifically polyoxyethylene sorbitan monooleates, etc.), polyethylene glycol fatty acid esters, and the like. More preferred examples thereof include polyethylene glycolated lipids.

Examples of the lipid derivative, fatty acid derivative or aliphatic hydrocarbon derivative of polyglycerin derivative include polyglycerolated lipids (specifically polyglycerin-phosphatidylethanolamines, etc.), polyglycerol fatty acid esters, and the like, and more preferred examples thereof include polyglycerolated lipids.

The amphiphilic substance used in the present invention has a difference of hydrophobic affinity, electrostatic interaction, etc. between a hydrophilic moiety and a hydrophobic moiety in the molecule, smaller than that of the lipid derivative, fatty acid derivative, or aliphatic hydrocarbon derivative of the water-soluble substance. Examples of such amphiphilic substances include phospholipids (having the same definition as above), glycoglycerolipids (having the same definition as above), glycosphingolipids (having the same definition as above), cholesterols (having the same definition as above), cationic lipids (having the same definition as above), anionic lipids (having the same definition as above, surfactants (having the same definition as above), and lipid derivatives, fatty acid derivatives or aliphatic hydrocarbon derivatives of water-soluble polymers (having the same definition as above), and further preferred examples thereof include the phospholipids, cholesterols, and surfactants.

The fine particles of the present invention comprising the lipid, fatty acid, or derivative thereof which are surface-modified with the water-soluble substance, can be produced by the method, which contains the Step A of dispersing the fine particles comprising the lipid, fatty acid, or derivative thereof, and dissolving or dispersing the surface modifier which is the lipid derivative, fatty acid derivative, or aliphatic hydrocarbon derivative of the water-soluble substance, in the liquid comprising a polar organic solvent. The fine particles are obtained in the form of a dispersion liquid. In the Step A, it is preferred that the amphiphilic substance is dissolved or dispersed in the liquid comprising a polar organic solvent. In the present invention, the term "the fine particles comprising the lipid, fatty acid, or derivative thereof are dispersed" means that the fine particles are suspended, emulsified or made into an emulsion, preferably suspended. A small part of the fine particles may be dissolved or deposited in the liquid, while a large part thereof is dispersed. It is preferred that all fine particles are dispersed in the liquid. The term "the surface modifier or the amphiphilic substance is dispersed" means that the surface modifier or the amphiphilic substance forms an aggregate, micelle, or the like and is suspended, emulsified or made into an emulsion, preferably emulsified. A small part of the surface modifier or the amphiphilic substance may be dissolved in the liquid, while a large part thereof forms the aggregate, micelle, or the like and is emulsified or made into an emulsion. Further, a small part of the surface modifier or the amphiphilic substance may be deposited in the liquid, while a large part thereof forms the aggregate, micelle, or the like and is suspended, emulsified or made into an emulsion, preferably emulsified and made into an emulsion. In the case of dispersing a component by mixing in the Step A, the mixing may be carried out by various industrially acceptable mixing methods without a particular apparatus. The component may be mixed in a storage vessel such as a tank or a vial, a transport tube, or a flow channel.

In the Step A, there are no particular limitations on the ratio of the polar organic solvent in the liquid as long as the fine particles comprising the lipid, fatty acid, or derivative thereof can be dispersed and the surface modifier can be dissolved or dispersed. The polar organic solvent concentration of the liquid is preferably such that the fine particles comprising the lipid, fatty acid, or derivative thereof are dispersed, and the surface modifier is dissolved, or dispersed by emulsified or made into an emulsion, in the liquid. The polar organic solvent concentration may be selected depending on the types of the solvent, the fine particles comprising the lipid, fatty acid, or derivative thereof, and the surface modifier, etc., and is preferably 80 vol % or less, more preferably 1 to 60 vol %, further preferably 5 to 55 vol %, most preferably 30 to 40 vol %.

In the present invention, there are no particular limitations on the combination of the polar organic solvent, with the fine particles comprising the lipid, fatty acid, or derivative thereof, the surface modifier, and the amphiphilic substance, and the combination is preferably such that the fine particles can be dispersed in the liquid comprising a polar organic solvent, and the surface modifier and the amphiphilic substance are soluble in the polar organic solvent. In the present invention, the surface modifier and the amphiphilic substance are soluble in the polar organic solvent in a case where the surface modifier and the amphiphilic substance can be dissolved per se in the polar organic solvent, in a case where the surface modifier and the amphiphilic substance can be dissolved by using a solubilizing agent or the like in the polar organic solvent, and in a case where the surface modifier and the amphiphilic substance can form an aggregate, a micelle, or the like to be suspended or emulsified in the polar organic solvent, etc. It is preferred that the surface modifier and the amphiphilic substance can be dissolved per se in the polar organic solvent.

In the method of the present invention, there are no particular limitations on the amount of each component. In the Step A, the concentration of the fine particles comprising the lipid, fatty acid, or derivative thereof in the liquid comprising a polar organic solvent is preferably 1 µg/mL to 1 g/mL, more preferably 0.1 to 500 mg/mL. The concentration of the surface modifier in the liquid is preferably 1 µg/mL to 1 g/mL, more preferably 0.1 to 400 mg/mL. Further, the weight ratio of the fine particles comprising the lipid, fatty acid, or derivative thereof which are surface-modified with the water-soluble substance, to the surface modifier of the present invention is preferably 1000:1 to 1:10, more preferably 100:1 to 1:1, further preferably 10:1 to 2:1. Furthermore, the weight ratio between the amphiphilic substance and the surface modifier of the present invention is preferably 10:1 to 1:100, more preferably 5:1 to 1:10. The weight ratio of the fine particles comprising the lipid, fatty acid, or derivative thereof which are surface-modified with the water-soluble substance, to the surface modifier is preferably 100:1 to 10:1 in some cases because of the safeness, cost, and the like of the surface modifier. In the cases, the weight ratio between the amphiphilic substance and the surface modifier is preferably 1:2 to 1:10.

The average particle diameter of the fine particles, comprising the lipid, fatty acid, or derivative thereof which are surface-modified with the water-soluble substance obtained by the method of the present invention, is preferably 300 nm or less, more preferably 200 nm or less, and for example, the size of the modified fine particles is preferably such that the modified fine particles can be administered by injection.

The fine particles comprising the lipid, fatty acid, or derivative thereof which are surface-modified with the water-soluble substance produced by the method of the present invention, can be used, for example, as a pharmaceutical preparation intended for stabilizing a drug in a living body component such as blood component (e.g., blood or digestive fluid), reducing a side effect, increasing accumulation of a drug in a target organ of a tumor, etc., improving absorption of a medicine in oral or transmucosal administration, or the like.

In a case where at least one constituent component of the fine particles to be modified is a drug, the fine particles comprising the lipid, fatty acid, or derivative thereof which are surface-modified with the water-soluble substance produced by the method of the present invention can be administered, for example, as a drug-comprising carrier for carrying the drug to a tumor or inflammation site, and thus the drug can be delivered to the tumor or inflammation site. When the drug is the antitumor drug, the modified fine particles can be administered as a tumor therapeutic agent for treating tumor. When the drug is the anti-inflammatory drug, the modified fine particles can be administered as a therapeutic agent for treating inflammation. Further, a tissue or organ in which neovascularization is enhanced is one of the sites in which the modified fine particles comprising the lipid, fatty acid, or derivative thereof which are surface-modified with the water-soluble substance produced by the method of the present invention can be delivered. When at least one constituent component of the fine particles to be modified is a therapeutic drug for a disease in the tissue or organ, the fine particles can be administered as a therapeutic agent for treating the disease.

In the case of using the fine particles comprising the lipid, fatty acid, or derivative thereof which are surface-modified with the water-soluble substance produced by the method of the present invention, the dispersion liquid of the fine particles comprising the lipid, fatty acid, or derivative thereof which are surface-modified with the water-soluble substance prepared in the above manner may be used as it is in the form of an injection preparation, etc. The dispersion liquid may be subjected to filtration, centrifugation, or the like to remove the solvent. Further, the dispersion liquid, to which an excipient such as mannitol, lactose, trehalose, maltose, or glycine is added, may be subjected to lyophilization.

In the case of an injection preparation, it is preferred that an injection preparation is prepared by mixing, for example, water, an acid, an alkali, a various buffer solution, a physiological saline solution, an amino acid transfusion, or the like, with the dispersion liquid of the fine particles comprising the lipid, fatty acid, or derivative thereof which are surface-modified with the water-soluble substance or the fine particles obtained by removing the solvent or by lyophilization. Further, it is possible to prepare an injection preparation by adding an antioxidant such as citric acid, ascorbic acid, cysteine or EDTA, an isotonic agent such as glycerol, glucose, sodium chloride or the like. Further, it can also be cryopreserved by adding a cryopreservation agent such as glycerol.

The fine particles of the invention comprising the lipid, fatty acid, or derivative thereof which are surface-modified with the water-soluble substance, may be subjected to granulation, drying, etc. together with an appropriate excipient or the like, to generate an oral preparation such as a capsule, a tablet, or a granule.

A kit may be used in the producing method of the invention. The kit may comprise, for example, the fine particles comprising the lipid, fatty acid, or derivative thereof, the surface modifier which is the fatty acid derivative or aliphatic hydrocarbon derivative of the water-soluble substance, and the liquid comprising a polar organic solvent. For example, the fine particles, comprising the lipid, fatty acid, or derivative thereof which are surface-modified with the water-soluble substance, can be prepared by the method of the invention using the kit such that the fine particles comprising the lipid, fatty acid, or derivative thereof; the surface modifier which is the fatty acid derivative or aliphatic hydrocarbon derivative of the water-soluble substance, and the liquid comprising a polar organic solvent are filled in small vessels respectively, and preferably the amphiphilic substance or the like is filled in another small vessel, and the components are mixed. There are no limitations on the mixing of the components, such as a limitation that the components have to be mixed under heating, and thus the kit is advantageous in that the fine particles can be easily prepared. The constituent components used in the kit may be in any state such as the solution state or the lyophilization state. The constituent components may be combined before introducing the components into the kit, and it is preferred the fine particles comprising the lipid, fatty acid, or derivative thereof and the surface modifier which is the fatty acid derivative or aliphatic hydrocarbon derivative of the water-soluble substance are placed separately, and the amphiphilic substance is combined to the surface modifier.

The producing method of the present invention may comprise a heating step. In the case of producing a preparation comprising a drug such as a protein or a nucleic acid, or the like as a constituent component, the activity of the drug or the like can be adversely affected by just heating for a short period of time. Thus, it is preferred that the drug or the like is heated at a lower temperature, at which the activity is not affected, for a short period of time. The siRNA comprises a short-chain RNA forming a complementary double strand, and is dissociated into single strands under heating at 60° C. or higher. When the single strands are then cooled, a single-stranded RNA or an incompletely complementary RNA having a nonspecific double strand is generated in some cases, and such RNAs are easily decomposed by a degradative enzyme. Further, it is considered that the single-stranded siRNA cannot form an RISC complex for recognizing an mRNA.

The fine particles comprising the lipid, fatty acid, or derivative thereof which are surface-modified with the water-soluble substance, can be prepared by the producing method of the present invention without the heating step. The method is advantageous in that, even in a case where a preparation comprising a drug such as a protein or nucleic acid which is easily affected by heat, the modified fine particles can be prepared at a low temperature, at which the activity of the drug is not affected. Further, the method is advantageous in that the phase transition of liposome membrane forming substance or the like is easily caused even at a low temperature due to the polar organic solvent. Thus, even in a case where the fine particles comprising the lipid, fatty acid, or derivative thereof has a high phase transition temperature, or in a case where the surface modifier has a low critical micelle concentration, the fine particles comprising the lipid, fatty acid, or derivative thereof which are surface-modified with the water-soluble substance, can be produced without the heating step. In the producing-method of the present invention, it is preferred that the amphiphilic substance is dissolved or dispersed together with the surface modifier which is the lipid derivative, fatty acid derivative, or aliphatic hydrocarbon derivative of the water-soluble substance. The amphiphilic substance acts to further improve the productivity such as yield of the fine particles comprising the lipid, fatty acid, or derivative thereof which are surface-modified with the water-soluble substance, and acts to improve the stability and the function such as retention in blood.

The present invention will be specifically described below with reference to Examples. Methods of producing the fine particles surface-modified with the water-soluble substance, described in Examples, are a method wherein the fine particles comprising the lipid, fatty acid, or derivative thereof are liposome, the polar organic solvent is ethanol, the amphiphilic substance is a phospholipid, and the surface modifier is a polyethylene glycolated lipids, and a method wherein the fine particles comprising the lipid, fatty acid, or derivative thereof are liposome, the polar organic solvent is ethanol, the amphiphilic substance is a phospholipid, and the surface modifier is a polyethylene glycol fatty acid ester. The invention will be specifically described below with reference to Examples without intention of restricting the scope of the invention.

Reference Example 1

Preparation of Modification Target Particles 5 mg of dextran fluorescein anionic (FD, available from Molecular Probes, Inc.), 30 mg of DOTAP (available from Avanti Polar Lipids, Inc., the same applies in the following examples), and 12 mg of PEG-DSPE (available from NOF Corporation, the same applies in the following examples) were dispersed in 1 mL of an injection water (available from Otsuka Pharmaceutical Co., Ltd., the same applies in the following examples). The dispersion liquid was passed through a polycarbonate membrane having a pore diameter of 0.4 μm (available from Whatman, Inc., the same applies in the following examples) 10 times, and passed through a polycarbonate membrane having a pore diameter of 0.1 μm (available from Whatman, Inc., the same applies in the following examples) 10 times. 500 μL of the obtained dispersion liquid was mixed with 60 mg of EPC (available from NOF Corporation, the same applies in the following examples), 12.5 mg of PEG-DSPE, and 2000 μL of a mixed solvent of ethanol/water (8/5), to obtain a dispersion liquid of modification target particles.

[Table 1]

TABLE 1

| Composition of modification target particles | |
|---|---|
| FD | 2.5 mg |
| DOTAP | 15 mg |
| PEG-DSPE | 18.5 mg |
| EPC | 60 mg |
| Mixed solvent of ethanol/water (about 1:1) | 2500 μL |

Example 1

Water was added dropwise to the dispersion liquid of modification target particles prepared in Reference Example 1 such that the ethanol concentration was about 40 vol %. The resulting liquid was mixed with a liquid prepared by dispersing a surface modifier of PEG-DSPE (7.5 mg) in 150 μL of a mixed solvent of ethanol/water (2/3). An appropriate amount of water was further added dropwise thereto such that the ethanol concentration was about 5 vol %, the obtained liquid was subjected to ultracentrifugation (1 hour, 110,000×g, 25° C.), the supernatant was removed, and a phosphate buffered saline (PBS) was added to the residue to obtain a preparation.

Example 2

A preparation was obtained in the same manner as Example 1 except that 25 mg of PEG-DSPE was used as a surface modifier.

Example 3

A preparation was obtained in the same manner as Example 1 except that 7.5 mg of PEG-DSPE was used as a surface modifier in combination with 7.5 mg of EPC as an amphiphilic substance.

Example 4

A preparation was obtained in the same manner as Example 1 except that 25 mg of PEG-DSPE was used as a surface modifier in combination with 25 mg of EPC as an amphiphilic substance.

Example 5

A preparation was obtained in the same manner as Example 1 except that 7.5 mg of PEG-DSPE was used as a surface modifier in combination with 22.5 mg of EPC as an amphiphilic substance.

Comparative Example 1

Water was added dropwise to the dispersion liquid of modification target particles prepared in Reference Example 1 such that the ethanol concentration was about 5 vol %. The obtained liquid was subjected to ultracentrifugation (1 hour, 110,000×g, 25° C.), the supernatant was removed, and PBS was added to the residue to obtain a preparation.

Comparative Example 2

Water was added dropwise to the dispersion liquid of modification target particles prepared in Reference Example 1 such that the ethanol concentration was about 5 vol %. The obtained liquid was subjected to ultracentrifugation (1 hour, 110,000×g, 25° C.), the supernatant was removed, and PBS (1440 μL) comprising PEG-DSPE (12.5 mg) and EPC (12.5 mg) was added to the residue to obtain a preparation.

Comparative Example 3

Water was added dropwise to the dispersion liquid of modification target particles prepared in Reference. Example 1 such that the ethanol concentration was about 5 vol %. The obtained liquid was subjected to ultracentrifugation (1 hour, 110,000×g, 25° C.), the supernatant was removed, PBS was added to the residue to adjust the EPC concentration at 24 mg/mL, and the liquid was heated at 70° C. for 1 minute. PEG-DSPE (5 mg) was added to 1 mL of the obtained liquid, and the mixture was heated at 70° C. for 2 minutes to obtain a preparation.

Test Example 1

The average particle diameter, recovery rates of FD and EPC, and blood kinetics of each of the preparations obtained in Examples 1 to 5 and Comparative Examples 1 to 3 were examined by the following methods. The results are shown in Table 2 and FIG. 1.

Average Particle Diameter

The average particle diameter of the coated fine particles which are surface-modified with a water-soluble substance in a preparation was measured by a dynamic light scattering method (DLS) using an apparatus A MODEL ELS-800 (manufactured by Otsuka Electronics, Co., Ltd., the same applies in the following examples).

Recovery Rates of FD and EPC

Each preparation was diluted with PBS such that the total lipid concentration was 30 mg/mL, and was further diluted 1,000-fold with PBS. 50 µL of 10-w/v % TRITON X-100 (available from Wako Pure Chemical Industries, Ltd., the same applies in the following examples) and PBS (400 µL) were added to each of the diluted liquid (50 µL), and stirred by a vortex mixer. The supernatant obtained by the ultracentrifugation in each of above Examples and Comparative Examples was diluted 10-fold with PBS, and 10-w/v % TRITON X-100 (50 µL) and PBS (400 µL) were added to each of the diluted liquid (50 µL), and stirred by a vortex mixer. 100 µL of thus-obtained liquids were placed on a 96-well microplate respectively, and the fluorescence intensities thereof were measured at an excitation wavelength of 485 nm and a fluorescence wavelength of 530 nm using a fluorescence plate reader (ARVOsx-4 manufactured by Wallac, the same applies in the following examples). Meanwhile, the fluorescence intensities of FD-PBS liquids having concentrations of 1, 0.5, and 0.25 µg/mL were measured respectively, to obtain a calibration curve. The FD concentration of each preparation was obtained using the calibration curve. Further, the EPC concentration of each preparation was obtained by using Phospholipid C-TEST WAKO (available from Wako Pure Chemical Industries, Ltd., the same applies in the following examples).

The recovery rate of FD and recovery rate of EPC of each preparation were calculated using the following equations (1) and (2).

[Equation 1]

$$\text{Recovery rate of FD (\%)} = A_1/(A_1+B_1) \times 100 \quad (1)$$

$A_1$: FD content of preparation (µg)=Concentration of FD in preparation (µg/mL)×Volume of preparation (mL)
$B_1$: FD content of supernatant (µg)=concentration of FD in supernatant (µg/mL)×Volume of supernatant (mL)

[Equation 2]

$$\text{Recovery rate of EPC (\%)} = A_2/(A_2+B_2) \times 100 \quad (2)$$

$A_2$: EPC content of preparation (µg)=Concentration of EPC in preparation (µg/mL)×Volume of preparation (mL)
$B_2$: EPC content of supernatant (µg)=Concentration of EPC in supernatant (µg/mL)×Volume of supernatant (mL)

Evaluation of Blood Kinetics

Each preparation was diluted with PBS such that the total lipid concentration was 5 mg/mL, and administered to a rat at a lipid/rat weight ratio of 10 mg/kg. The blood samples were collected from the rat 1 minute, 10 minutes, 30 minutes, 1 hour, 3 hours, 6 hours, and 24 hours after the administration, and were subjected to centrifugation to obtain plasmas, respectively. To determine the FD content of each plasma, 10 w/v % TRITON X-100 (50 µL) and PBS (400 µL) were added to 50 µL of the plasma and stirred by a vortex mixer. 100 µL of thus-obtained liquids were placed on a 96-well microplate respectively, and the fluorescence intensities thereof were measured at an excitation wavelength of 485 nm and a fluorescence wavelength of 530 nm using ARVOsx-4. Meanwhile, the fluorescence intensities of FD-PBS liquids having concentrations of 1, 0.5, and 0.25 µg/mL were measured respectively, to obtain a calibration curve. The FD concentration of plasma was obtained using the calibration curve. The plasma amount per 100-g rat weight was considered as 7.8 mL, and thus the drug retention in blood (%) to the administration dose was calculated, and $AUC_{0\text{-}24\,h}$ (µg·min/dose) was calculated by trapezoidal method.

TABLE 2

| | PEG-DSPE (mg) | EPC (mg) | Average particle diameter (nm) | Recovery rate (%) FD | Recovery rate (%) EPC | AUC (µg·min/dose) |
|---|---|---|---|---|---|---|
| Ex. 1 | 7.5 | 0 | 122 | 95 | 90 | 195 |
| Ex. 2 | 25 | 0 | 144 | 76 | 82 | 385 |
| Ex. 3 | 7.5 | 7.5 | 133 | 87 | 90 | 363 |
| Ex. 4 | 25 | 25 | 146 | 87 | 87 | 464 |
| Ex. 5 | 7.5 | 22.5 | 177 | 94 | 94 | 315 |
| Comp. Ex. 1 | 0 | 0 | 138 | 93 | 93 | 74 |
| Comp. Ex. 2 | 12.5 | 12.5 | 141 | 93 | 92 | 90 |
| Comp. Ex. 3 | 12.5 | 0 | 194 | 94 | 90 | 355 |

As shown in Table 2, the preparations obtained in Examples 1 to 5 exhibited excellent retentions in blood depending on the amounts of the surface modifier (PEG-DSPE), equal to that of Comparative Example 3 and higher than those of Comparative Examples 1 and 2. Further, the preparations obtained in Examples 3 and 4 using the amphiphilic substance (EPC) in combination with the surface modifier exhibited more excellent retentions in blood, higher than those of the preparations obtained in Examples 1 and 2 not using the amphiphilic substance. Although the method of the present invention is simpler and without a limitation that the components have to be heated, etc., the fine particles comprising the lipid, fatty acid, or derivative thereof which were surface-modified with the water-soluble substance, were superior to the fine particles obtained in water at room temperature by the conventional method, and equal or superior to the fine particles obtained in water under heating by the conventional method, can be obtained.

Example 6

Water was added dropwise to the dispersion liquid of modification target particles prepared in Reference Example 1 such that the ethanol concentration was about 2.5 vol %. The obtained liquid was mixed with a liquid prepared by dispersing PEG-DSPE (12.5 mg) as a surface modifier and EPC (12.5 mg) as an amphiphilic substance in 2,400 µL of a mixed solvent of ethanol/water (1/39). The obtained liquid was subjected to ultracentrifugation (1 hour, 110,000×g, 25° C.), the supernatant was removed, and PBS was added to the residue to obtain a preparation.

Example 7

Water was added dropwise to the dispersion liquid of modification target particles prepared in Reference Example 1 such that the ethanol concentration was about 5 vol %. The obtained liquid was mixed with a liquid prepared by dispersing PEG-DSPE (12.5 mg) as a surface modifier and EPC (12.5 mg) as an amphiphilic substance in 400 µL of a mixed solvent of ethanol/water (1/19). The obtained liquid was subjected to ultracentrifugation (1 hour, 110,000×g, 25° C.), the supernatant was removed, and PBS was added to the residue to obtain a preparation.

Example 8

Water was added dropwise to the dispersion liquid of modification target particles prepared in Reference Example 1 such that the ethanol concentration was about 30 vol %. The obtained liquid was mixed with a liquid prepared by dispersing PEG-DSPE (12.5 mg) as a surface modifier and EPC (12.5 mg) as an amphiphilic substance in 200 μL of a mixed solvent of ethanol/water (3/7). An appropriate amount of water was further added dropwise thereto such that the ethanol concentration was about 5 vol %, the obtained liquid was subjected to ultracentrifugation (1 hour, 110,000×g, 25° C.), the supernatant was removed, and PBS was added to the residue to obtain a preparation.

Example 9

The dispersion liquid of modification target particles prepared in Reference Example 1 was mixed with a liquid prepared by dispersing PEG-DSPE (12.5 mg) and EPC (12.5 mg) as an amphiphilic substance in 200 μL of a mixed solvent of ethanol/water (1/1). An appropriate amount of water was further added dropwise thereto such that the ethanol concentration was about 5 vol %, the obtained liquid was subjected to ultracentrifugation (1 hour, 110,000×g, 25° C.), the supernatant was removed, and PBS was added to the residue to obtain a preparation.

Test Example 2

Figure 2:
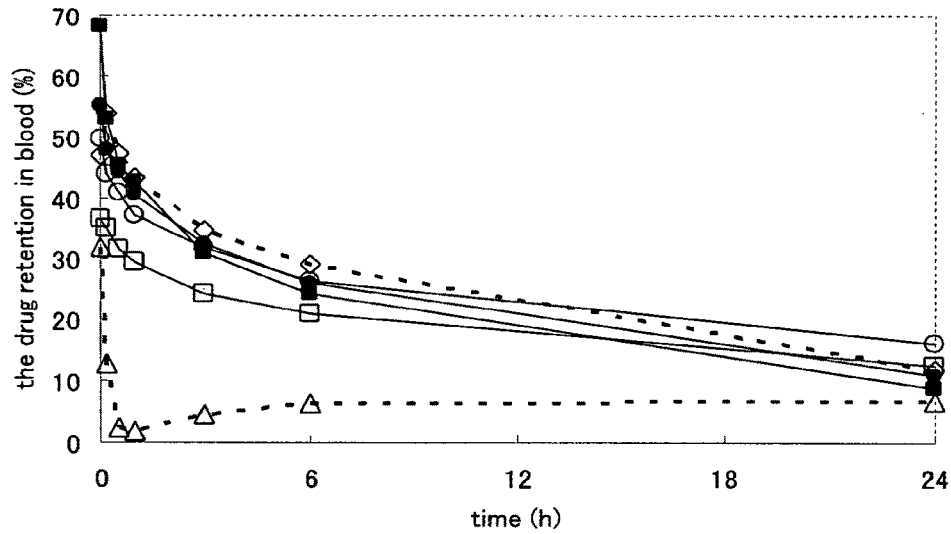
FIG. 2 Blood kinetics of preparations obtained in Examples 6 to 9 and Comparative Examples 2 and 3 after administering them to rats are shown. The closed squares represent administration results of the preparation of Example 6, the open squares represent administration results of the preparation of Example 7, the closed circles represent administration results of the preparation of Example 8, the open circles represent administration results of the preparation of Example 9, the open triangles represent administration results of the preparation of Comparative Example 2 and the open diamonds represent administration results of the preparation of Comparative Example 3.

The average particle diameter, recovery rates of FD and EPC, and blood kinetics of each of the preparations obtained in Examples 6 to 9 were examined in the same manner as Test Example 1. The results are shown in Table 3 and FIG. 2.

TABLE 3

| | Ethanol concentration (approx. vol %) | Average particle diameter (nm) | Recovery rate (%) | | AUC (μg · min/dose) |
|---|---|---|---|---|---|
| | | | FD | EPC | |
| Ex. 6 | 2.5 | 159 | 91 | 80 | 304 |
| Ex. 7 | 5 | 137 | 94 | 94 | 273 |
| Ex. 8 | 30 | 156 | 91 | 87 | 324 |
| Ex. 9 | 50 | 147 | 94 | 95 | 349 |
| Comp. Ex. 2 | 0 | 141 | 93 | 92 | 90 |
| Comp. Ex. 3 | 0 | 194 | 94 | 90 | 355 |

As shown in Table 3, the preparations obtained in Examples 6 to 9 exhibited excellent retentions in blood, equal to that of Comparative Example 3 and higher than that of Comparative Example 2.

Reference Example 2

Preparation of Modification Target Particles

DOTAP and PEG-DSPE were dispersed in water at concentrations of 30 and 12 mg/mL, respectively. The dispersion liquid was passed through a polycarbonate membrane having a pore diameter of 0.4 μm 10 times, and passed through a polycarbonate membrane having a pore diameter of 0.1 μm 10 times. 500 μL of the obtained dispersion liquid was mixed with 250 μL of a 15-mg/mL aqueous solution of ODN (fluorescein isothiocyanate-labeled, phosphorothioate oligodeoxyribonucleotide, having a sequence of (5')CCT CTT ACC TCA G(3'), a base number of 13, and a molecular weight of 4573.57, available from SciMedia Ltd.), and was further mixed with 50 μL of a solution prepared by dissolving EPC and PEG-DSPE in ethanol (1,000 μL) at concentrations of 120 and 25 mg/mL respectively, to obtain a dispersion liquid of modification target particles.

Example 10

Water was added dropwise to the dispersion liquid of modification target particles prepared in Reference Example 2 such that the ethanol concentration was about 50%. 1,000 μL of a 50% aqueous ethanol comprising PEG-DSPE (12.5 mg) as a surface modifier and EPC (2.5 mg) as an amphiphilic substance was added to the obtained liquid, and an appropriate amount of water was further added dropwise thereto such that the ethanol concentration was 5 vol %. The obtained liquid was subjected to ultracentrifugation (1 hour, 110,000×g, 25° C.), the supernatant was removed, and PBS was added to the residue to obtain a preparation.

Example 11

A preparation was obtained in the same manner as Example 10 except that 12.5 mg of PEG-DSPE was used as a surface modifier in combination with 12.5 mg of EPC as an amphiphilic substance.

Test Example 3

Figure 3:
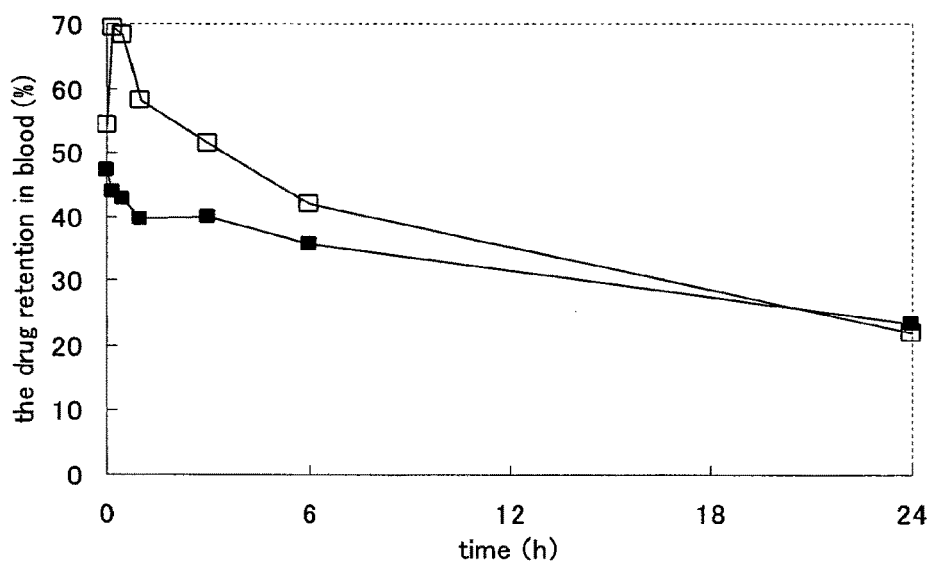
FIG. 3 Blood kinetics of preparations obtained in Examples 10 and 11 after administering them to rats are shown. The closed squares represent administration results of the preparation of Example 10 and the open squares represent administration results of the preparation of Example 11.

The average particle diameter, recovery rates of ODN and EPC, and blood kinetics of each of the preparations obtained in Examples 10 and 11 were examined in the following manner. The results are shown in Table 4 and FIG. 3.
Average Particle Diameter
The average particle diameter of the fine particles which were surface-modified with the water-soluble substance in each preparation was measured by DLS.
Recovery Rates of ODN and EPC
Each preparation was diluted with PBS such that the total lipid concentration was 30 mg/mL, and was further diluted 1,000-fold with PBS. 10-w/v % TRITON X-100 (50 μL) and PBS (400 μL) were added to 50 μL of the diluted liquid, and stirred by a vortex mixer. The supernatant obtained by the ultracentrifugation in each of above Examples was diluted 10-fold with PBS, and 10-w/v % TRITON X-100 (50 μL) and PBS (400 μL) were added to 50 μL of the diluted liquid, and stirred by a vortex mixer. 100 μL of thus-obtained liquids were placed on a 96-well microplate respectively, and the fluorescence intensities thereof were measured at an excitation wavelength of 485 nm and a fluorescence wavelength of 530 nm using ARVOsx-4. Meanwhile, the fluorescence intensities of ODN-PBS liquids having concentrations of 1.5, 1.5/4, $1.5/4^2$, $1.5/4^3$, $1.5/4^4$ and $1.5/4^5$ μg/mL were measured respectively, to obtain a calibration curve. The ODN concentration of each preparation was obtained using the calibration curve. Further, the EPC concentration of each preparation was obtained by using Phospholipid C-TEST WAKO.

The recovery rate of ODN and recovery rate of EPC of each preparation were calculated using the following equations (3) and (4).
[Equation 3]

$$\text{Recovery rate of ODN (\%)} = A_3/(A_3+B_3) \times 100 \qquad (3)$$

$A_3$: ODN content of preparation (μg)=concentration of ODN in preparation (μg/mL)×Volume of preparation (mL)
$B_3$: ODN content of supernatant (μg)=concentration of ODN in supernatant (μg/mL)×Volume of supernatant (mL)
[Equation 4]

$$\text{Recovery rate of EPC (\%)} = A_4/(A_4+B_4) \times 100 \qquad (4)$$

$A_4$: EPC content of preparation (μg)=concentration of EPC in preparation (μg/mL)×Volume of preparation (mL)

$B_4$: EPC content of supernatant (μg)=concentration of EPC in supernatant (μg/mL)×Volume of supernatant (mL)

Evaluation of Blood Kinetics

Each preparation was diluted with PBS such that the total lipid concentration was 5 mg/mL, and administered to a rat at a lipid/rat weight ratio of 10 mg/kg. The blood samples were collected from the rat 1 minute, 10 minutes, 30 minutes, 1 hour, 3 hours, 6 hours, and 24 hours after the administration, and were subjected to centrifugation to obtain plasmas, respectively. To determine the ODN content of each plasma, 10 w/v % TRITON X-100 (50 μL) and PBS (400 μL) were added to 50 μL of the plasma and stirred by a vortex mixer. 100 μL of thus-obtained liquids were placed on a 96-well microplate respectively, and the fluorescence intensities thereof were measured at an excitation wavelength of 485 nm and a fluorescence wavelength of 530 nm using ARVOsx-4. Meanwhile, the fluorescence intensities of ODN-PBS liquids having concentrations of 1.5, 1.5/4, 1.5/$4^2$, 1.5/$4^3$, 1.5/$4^4$, and 1.5/$4^5$ μg/mL were measured respectively, to obtain a calibration curve. The ODN concentration of plasma was obtained using the calibration curve. The plasma amount per 100-g rat weight was considered as 7.8 mL, and thus the drug retention in blood (%) to the administration dose was calculated, and $AUC_{0\text{-}24\ h}$ (μg·min/dose) was calculated by trapezoidal method.

TABLE 4

| | Ethanol concentration (approx. vol %) | PEG-DSPE (mg) | EPC (mg) | Average particle diameter (nm) | Recovery rate (%) ODN | Recovery rate (%) EPC | AUC (μg · min/dose) |
|---|---|---|---|---|---|---|---|
| Ex. 10 | 50 | 12.5 | 2.5 | 118 | 91 | 39 | 460 |
| Ex. 11 | 50 | 12.5 | 12.5 | 113 | 97 | 74 | 533 |

As shown in Table 4, the preparations obtained in Examples 10 and 11 exhibited excellent stable retentions in blood even though the modification target particles contained the ODN drug having a relatively high molecular weight.

Reference Example 3

Preparation of Modification Target Particles

A dextran fluorescein anionic (FD, 10 mg), DOTAP (60 mg) and PEG-DSPE (24 mg) were dispersed in 2 mL of water. The dispersion liquid was passed through a polycarbonate membrane having a pore diameter of 0.4 μm 10 times, and passed through a polycarbonate membrane having a pore diameter of 0.1 μm 10 times. Separately EPC (240 mg) and PEG-DSPE (50 mg), were dissolved in 8,000 μL of a mixed solvent of ethanol/water (5/3). 500 μL of the obtained dispersion liquid was mixed with 2,000 μL of the obtained solution of EPC and PEG-DSPE, to obtain a dispersion liquid of modification target particles.

TABLE 5

| Composition of modification target particles | |
|---|---|
| FD | 0.75 mg |
| DOTAP | 4.5 mg |
| PEG-DSPE | 5.55 mg |
| EPC | 18 mg |
| Mixed solvent of ethanol/water (about 1/1) | 750 μL |

Example 12

Water was added dropwise to 750 μL of the dispersion liquid of modification target particles prepared in Reference Example 3 such that the ethanol concentration was about 40 vol %. The obtained liquid was mixed with a liquid prepared by dispersing 7.5 mg of a polyethylene glycol monostearate 25 E.O. (PEG(25)-St, available from Nikko Chemicals Co., Ltd., the same applies in the following examples) as a surface modifier and 7.5 mg of EPC as an amphiphilic substance in 45 μL of a mixed solvent of ethanol/water (2/3). An appropriate amount of water was further added dropwise to the mixture such that the ethanol concentration was about 5 vol %. The obtained liquid was subjected to ultracentrifugation (1 hour, 110,000×g, 25° C.), the supernatant was removed, and PBS was added to the residue to obtain a preparation.

Example 13

A preparation was obtained in the same manner as Example 12 except that 7.5 mg of a polyethylene glycol monostearate 40 E.O. (PEG(40)-St, available from Nikko Chemicals Co., Ltd., the same applies in the following examples) was used as a surface modifier in combination with 7.5 mg of EPC as an amphiphilic substance.

Example 14

A preparation was obtained in the same manner as Example 12 except that 7.5 mg of PEG(40)-St was used as a surface modifier in combination with 3.75 mg of EPC as an amphiphilic substance.

Example 15

750 μL of the dispersion liquid of modification target particles prepared in Reference Example 3 was mixed with a liquid prepared by dispersing PEG(40)-St (7.5 mg) as a surface modifier and EPC (7.5 mg) as an amphiphilic substance in 60 μL of a mixed solvent of ethanol/water (1/1). An appropriate amount of water was further added dropwise to the mixture such that the ethanol concentration was about 5 vol %. The obtained liquid was subjected to ultracentrifugation (1 hour, 110,000×g, 25° C.), the supernatant was removed, and PBS was added to the residue to obtain a preparation.

Test Example 4

Figure 4:
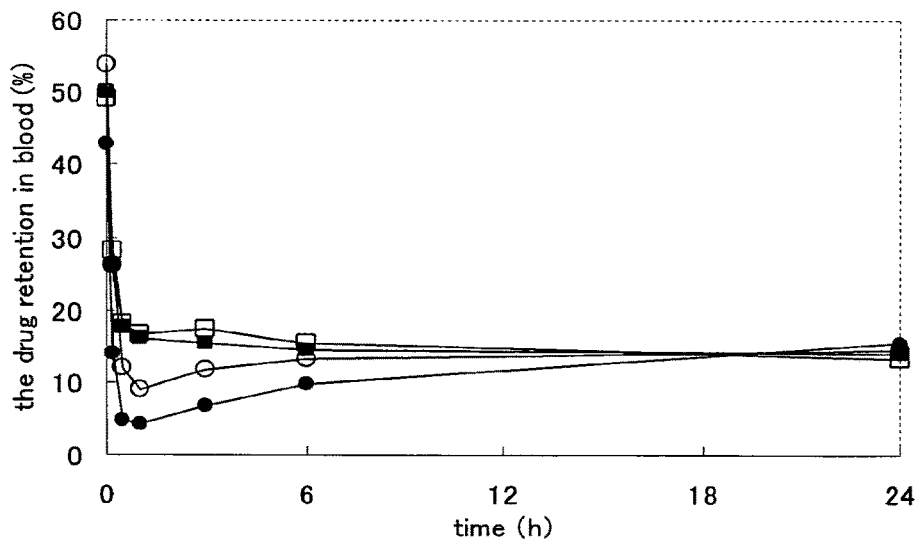
FIG. 4 Blood kinetics of preparations obtained in Examples 12 and 15 after administering them to rats are shown. The closed squares represent administration results of the preparation of Example 12, the open squares represent administration results of the preparation of Example 13, the closed circles represent administration results of the preparation of Example 14 and the open circles represent administration results of the preparation of Example 15.

The average particle diameter, recovery rates of FD and EPC, and blood kinetics of each of the preparations obtained in Examples 12 to 15 were examined in the same manner as Test Example 1. The results are shown in Table 6 and FIG. 4.

TABLE 6

| | Ethanol concentration (approx. vol %) | PEG-St (mg) | EPC (mg) | Average particle diameter (nm) | Recovery rate (%) FD | Recovery rate (%) EPC | AUC (µg · min/dose) |
|---|---|---|---|---|---|---|---|
| Surface modifier: PEG(25)-St | | | | | | | |
| Ex. 12 | 40 | 7.5 | 7.5 | 125 | 88 | 77 | 214 |
| Surface modifier: PEG(40)-St | | | | | | | |
| Ex. 13 | 40 | 7.5 | 7.5 | 135 | 93 | 85 | 219 |
| Ex. 14 | 40 | 7.5 | 3.75 | 123 | 90 | 76 | 164 |
| Ex. 15 | 50 | 7.5 | 7.5 | 111 | 73 | 64 | 195 |

As shown in Table 6, the preparations obtained in Examples 12 to 15 exhibited excellent retentions in blood even though the polyethylene glycol fatty acid esters were used as the surface modifier.

INDUSTRIAL APPLICABILITY

According to the present invention, there are provided a method of easily producing fine particles comprising a lipid, a fatty acid, or a derivative thereof surface-modified with a water-soluble substance, and the like. Further, there are provided a method of producing a fine particles comprising a lipid, a fatty acid, or a derivative thereof surface-modified with the water-soluble substance, which is capable of modifying various types of modification target particles substantially without heating, and the like.

The invention claimed is:

1. A method of modifying a surface of a fine particle with a water-soluble substance, comprising the steps of:
    (1) providing a liquid (a) comprising a fine particle, a surface modifier and an amphiphilic substance dispersed in a mixed solvent of an alcohol and water, wherein the mixed solvent is 45 to 80 vol % alcohol, wherein the average particle diameter of the fine particle is 300 nm or less, wherein the fine particle is selected from the group consisting of a liposome, a liposome assembly, and an emulsion particle, wherein the surface modifier has both a water-soluble substance moiety and a lipid, fatty acid or aliphatic hydrocarbon moiety, and wherein the surface modifier is one or more component(s) selected from polyethylene glycolated lipids, polyglycerolated lipids, polyethylene glycol alkyl ethers, polyethylene glycol sorbitan fatty acid esters, and polyethylene glycol fatty acid esters, and wherein the amphiphilic substance is one or more substance(s) selected from phospholipids, glyceroglycolipids, sphingoglycolipids, cholesterols, and cationic lipids,
    (2) adding water to the liquid (a) to reduce the alcohol concentration of the mixed solvent to about 40 vol % alcohol,
    (3) providing a liquid (b) comprising a surface modifier dispersed in a mixed solvent of an alcohol and water, wherein the mixed solvent is 30 to 80 vol % alcohol, wherein the surface modifier has both a water-soluble substance moiety and a lipid, fatty acid or aliphatic hydrocarbon moiety, and wherein the surface modifier is one or more component(s) selected from polyethylene glycolated lipids, polyglycerolated lipids, polyethylene glycol alkyl ethers, polyethylene glycol sorbitan fatty acid esters, and polyethylene glycol fatty acid esters,
    wherein liquid (a) and/or liquid (b) also comprise an amphiphilic substance dispersed therein, wherein the amphiphilic substance is one or more substance(s) selected from phospholipids, glyceroglycolipids, sphingoglycolipids, cholesterols, and cationic lipids,
    (4) mixing the liquid (a) with the liquid (b), to obtain a liquid mixture, and
    (5) adding water to the liquid mixture to obtain a liquid mixture containing about 5 vol % alcohol,
    wherein the surface of the fine particle is modified by the surface modifier.

2. The method according to claim 1, wherein the fine particle is a liposome, the alcohol is ethanol, the amphiphilic substance is a phospholipid, and the surface modifier is a polyethylene glycolated lipid.

3. The method according to claim 1, wherein the fine particle is a liposome, the alcohol is ethanol, the amphiphilic substance is a phospholipid, and the surface modifier is a polyethylene glycol fatty acid ester.

4. The method according to claim 1, wherein the weight ratio between the amphiphilic substance and the surface modifier in the liquid mixture is 5:1 to 1:10.

5. The method according to claim 1, wherein the weight ratio of the fine particle to the surface modifier in the liquid mixture is 10:1 to 2:1.

6. The method according to claim 1, wherein the average particle diameter of the fine particle is 200 nm or less.

7. The method according to claim 1, wherein the fine particle contains a drug.

8. The method according to claim 7, wherein the drug is selected from the group consisting of a protein, a peptide, a nucleic acid, a low-molecular compound, a saccharide, a polymer, a lipid compound, and a metal compound.

9. The method according to claim 7, wherein the fine particle has an electrostatic charge opposite that of the drug.

10. The method according to claim 1, wherein the liquid mixture contains 30 to 40 vol % alcohol.

11. The method according to claim 1, wherein the liquid mixture is further subjected to a step(s) of removing the alcohol, lyophilization, granulation, or drying.

12. The method according to claim 1, wherein the liquid mixture is processed to produce an oral preparation or an injection preparation.

13. The method according to claim 1, wherein the liquid mixture is produced without heating.

14. The method according to claim 1, wherein the alcohol is ethanol.

15. A method of modifying a surface of a fine particle with a water-soluble substance, comprising the steps of:
    providing an aqueous dispersion liquid comprising a fine particle, wherein the average particle diameter of the fine particle is 300 nm or less, and wherein the fine particle is selected from the group consisting of a liposome, a liposome assembly, and an emulsion particle,
    providing a mixed solvent liquid comprising a surface modifier and an amphiphilic substance in a mixed solvent, wherein the mixed solvent is an alcohol and water, wherein the mixed solvent is 45 to 80 vol % alcohol, wherein the surface modifier has both a water-soluble substance moiety and a lipid, fatty acid or aliphatic hydrocarbon moiety, wherein the surface modifier is one or more component(s) selected from polyethylene glycolated lipids, polyglycerolated lipids, polyethylene glycol alkyl ethers, polyethylene glycol sorbitan fatty acid esters, and polyethylene glycol fatty acid esters, and wherein the amphiphilic substance is one or more substance(s) selected from phospholipids, glyceroglycolipids, sphingoglycolipids, cholesterols, and cationic lipids, mixing the aqueous dispersion liquid and the mixed solvent liquid to obtain a liquid (a), adding water to the liquid (a) to reduce the alcohol concentration of the mixed solvent to about 40 vol % alcohol, providing a liquid (b) comprising a surface modifier dispersed in a mixed solvent of an alcohol and water, wherein the mixed solvent is 30 to 80 vol % alcohol, wherein the surface modifier has both a water-soluble substance moiety and a lipid, fatty acid or aliphatic hydrocarbon moiety, and wherein the surface modifier is one or more component(s) selected from polyethylene glycolated lipids, polyglycerolated lipids, polyethylene glycol alkyl ethers, polyethylene glycol sorbitan fatty acid esters, and polyethylene glycol fatty acid esters, wherein liquid (a) and/or liquid (b) also comprise an amphiphilic substance dispersed therein, wherein the amphiphilic substance is one or more substance(s) selected from phospholipids, glyceroglycolipids, sphingoglycolipids, cholesterols, and cationic lipids, mixing the liquid (a) with the liquid (b), to obtain a liquid mixture, and adding water to the liquid mixture to obtain a liquid mixture containing about 5 vol % alcohol, wherein the surface of the fine particle is modified by the surface modifier.

16. The method according to claim 15, wherein the fine particle is a liposome, the alcohol is ethanol, the amphiphilic substance is a phospholipid, and the surface modifier is a polyethylene glycolated lipid.

17. The method according to claim 15, wherein the fine particle is a liposome, the alcohol is ethanol, the amphiphilic substance is a phospholipid, and the surface modifier is a polyethylene glycol fatty acid ester.

18. The method according to claim 15, wherein the weight ratio between the amphiphilic substance and the surface modifier in the liquid mixture is 5:1 to 1:10.

19. The method according to claim 15, wherein the weight ratio of the fine particle to the surface modifier in the liquid mixture is 10:1 to 2:1.

20. The method according to claim 15, wherein the average particle diameter of the fine particle is 200 nm or less.

21. The method according to claim 15, wherein the fine particle contains a drug.

22. The method according to claim 21, wherein the drug is selected from the group consisting of a protein, a peptide, a nucleic acid, a low-molecular compound, a saccharide, a polymer, a lipid compound, and a metal compound.

23. The method according to claim 21, wherein the fine particle has an electrostatic charge opposite that of the drug.

24. The method according to claim 15, wherein the liquid mixture contains 30 to 40 vol % alcohol.

25. The method according to claim 15, wherein the liquid mixture is further subjected to a step(s) of removing the alcohol, lyophilization, granulation, or drying.

26. The method according to claim 15, wherein the liquid mixture is processed to produce an oral preparation or an injection preparation.

27. The method according to claim 15, wherein the liquid mixture is produced without heating.

28. The method according to claim 15, wherein the alcohol is ethanol.

* * * * *